United States Patent [19]

Wess et al.

[11] Patent Number: 4,745,120
[45] Date of Patent: May 17, 1988

[54] 3-PYRIDYL COMPOUNDS AND USE AS THROMBOXANE SYNTHETASE INHIBITORS

[75] Inventors: Günther Wess, Erlensee; Wilhelm Bartmann, Bad Soden am Taunus; Gerhard Beck, Frankfurt am Main; Hans-Hermann Lau, Bad Soden am Taunus, all of Fed. Rep. of Germany

[73] Assignee: Hoechst Aktiengesellschaft, Frankfurt, Fed. Rep. of Germany

[21] Appl. No.: 767,965

[22] Filed: Aug. 21, 1985

[30] Foreign Application Priority Data

Aug. 23, 1984 [DE] Fed. Rep. of Germany ....... 3431004

[51] Int. Cl.$^4$ .................. A61K 31/44; A61K 31/455; C07D 213/50; C07D 401/12
[52] U.S. Cl. ..................................... 514/277; 514/332; 514/333; 514/336; 514/341; 546/256; 546/263; 546/266; 546/278; 546/283; 546/284; 546/339; 546/340; 546/342; 546/344
[58] Field of Search ............... 546/339, 344, 340, 263, 546/342, 256, 266, 283, 284, 278; 568/325, 659; 514/277, 332, 333, 336, 341

[56] References Cited

U.S. PATENT DOCUMENTS 4,271,176 6/1981 Tanouchi et al. ................... 546/333
4,317,828 3/1982 Tanouchi et al. ................... 546/333
4,427,680 1/1984 Tanouchi et al. ................... 546/342

FOREIGN PATENT DOCUMENTS 0098690 10/1984 European Pat. Off. .
2445319 7/1980 France .

OTHER PUBLICATIONS

Glossary of Chemical Terms, Hampel and Hawley, Editors, p. 6.
Tanouchi et al., Highly Selective . . . Pyridine Derivatives, J. Med. Chem., 1981, 24, 1149–1155.

Primary Examiner—Henry R. Jiles
Assistant Examiner—Dale A. Bjorkman
Attorney, Agent, or Firm—Finnegan, Henderson, Farabow, Garrett & Dunner

[57] ABSTRACT

The present invention relates to new pyridines substituted in the 3-position, of the formula

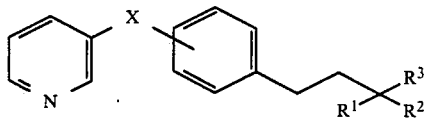

and to a process for their preparation. The compounds bring about specific inhibition of thromboxane synthetase and can thus be used as medicaments.

6 Claims, No Drawings

3-PYRIDYL COMPOUNDS AND USE AS THROMBOXANE SYNTHETASE INHIBITORS

Pyridine and certain derivatives are inhibitors of thromboxane synthetase (Miyamoto, T., Taniguchi, K., Tanouchi, T., and Hirata, F., Adv. Prostaglandin Thromboxane Res. 6, 443, (1980)).

The enzyme thromboxane synthetase catalyzes in the metabolism of arachidonic acid the conversion of prostaglandin endoperoxides ($PGH_2$ or $PGG_2$) into thromboxane $A_2$ ($TXA_2$). $TXA_2$ has high biological activity: it induces the aggregation of blood platelets and, moreover, has a powerful constricting action on smooth muscle. It plays an essential part in hemostasis, in pathological situations where there is an increased tendency to vasospasms and/or thrombosis. Furthermore, in vitro and in vivo $TXA_2$ has powerful contracting actions on bronchial muscle (B. Samuelsson, Angew. Chemie 95, 854 (1983)).

The new 3-pyridyl compounds which are described in the present invention are distinguished by a specific inhibitory effect on thromboxane synthetase.

Thus they are suitable for the prophylaxis or treatment of disorders where there is a disturbance (an increase) of the tendency of platelets to aggregate, and where there are pathologically raised levels of thromboxane, as are found with ischemia, angina pectoris, thromboembolic diseases, atherosclerosis, coronary spasms, arrhythmias, cerebral ischemic attacks, migraine and other vascular headaches, myocardial infarct, hypertension, breathing disturbances such as asthma and apnea, inflammatory disorders, and microvascular complications of diabetes mellitus. The compounds according to the invention have favorable effects on diseases where there are raised levels of thromboxane in various organs, for example in the region of the kidneys or in the gastrointestinal region associated with colitis or inflammatory bowel disease. In addition, some of the compounds according to the invention have pronounced hypolipidemic effects with preferential reduction in the atherogenic LDL and VLDL lipoprotein fractions. Hence they are suitable as lipid-lowering agents and for the treatment of arteriosclerosis. The present invention relates to new pyridines substituted in position 3, of the formula I, which bring about specific inhibition of thromboxane synthetase.

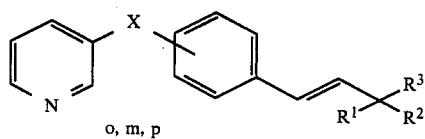

In the general formula I, X denotes a vinylene group or ethylene group, $R^1$ and $R^2$ together with the carbon atom to which they are attached denote the carbonyl group, or $R^1$ denotes hydrogen and $R^2$ denotes the radical —$OR^4$, in which $R^4$ represents hydrogen or (a) a branched or unbranched aliphatic acyl radical having up to 10 carbon atoms,
(b) the benzylcarbonyl or benzoyl radical, the phenyl radical being unsubstituted or substituted once to 3 times by halogen or $C_1$-$C_4$-alkyl,
(c) the radical

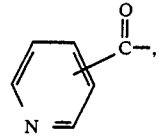

(d) branched or unbranched alkyl having 1–10 carbon atoms,
(e) the benzyl radical, the phenyl nucleus being unsubstituted or substituted once to 3 times by halogen or $C_1$-$C_4$-alkyl, or
(f) the radical

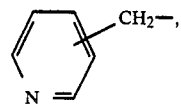

$R^3$ denotes a phenyl radical which can be substituted in the nucleus once to 3 times by halogen, trifluoromethyl, and/or alkyl or alkoxy having 1–6 carbon atoms, or a cycloaliphatic radical having 3–8 carbon atoms, a straight-chain or branched alkyl radical having up to 8 carbon atoms, a straight-chain or branched unsaturated aliphatic hydrocarbon radical having 3–8 carbon atoms, it being possible for the aliphatic radicals in turn to be substituted by (a) a straight-chain or branched alkoxy radical having up to 10 carbon atoms, or a cycloalkoxy radical having up to 6 carbon atoms, or a straight-chain or branched alkenyloxy or alkynyloxy radical having 3 to 6 carbon atoms,
(b) halogen, cycloalkyl having 3–7 carbon atoms, an unsubstituted phenyl, α- or β-thienyl or α- or β-furyl radical, or a phenyl, thienyl or furyl radical which in turn is substituted in the nucleus once to 3 times by halogen, trifluoromethyl and/or alkyl or alkoxy having 1–6 carbon atoms,
(c) an unsubstituted phenoxy, α- or β-thienyloxy or cycloalkoxy radical having 3–7 carbon atoms, or one of the radicals mentioned, which in turn is substituted in the nucleus once to 3 times by halogen, trifluoromethyl and/or alkyl or alkoxy each having 1–6 carbon atoms,
(d) a heteroaryl radical.

The substituents preferably have the following meaning:

$R^1$ and $R^2$ together with the carbon atom to which they are attached the carbonyl group, or $R^1$ hydrogen and $R^2$ the radical —$OR^4$, in which $R^4$ represents hydrogen or (a) branched or unbranched alkanoyl having up to 6 carbon atoms,
(b) the benzylcarbonyl or benzoyl radical, the phenyl radical being unsubstituted or substituted once by fluorine, chlorine or methyl,
(c) the radical

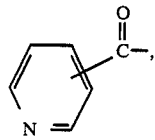

(d) branched or unbranched alkyl having 1-6 carbon atoms,
(e) the benzyl radical, the phenyl nucleus being unsubstituted or substituted once by chlorine, fluorine or methyl, or
(f) the radical

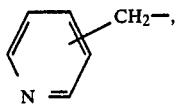

$R^3$ a cycloaliphatic radical having 3-8 carbon atoms, a straight-chain or branched alkyl radical having up to 8 carbon atoms, a straight-chain or branched unsaturated aliphatic hydrocarbon radical having 3 to 8 carbon atoms, it being possible for the aliphatic radicals in turn to be substituted by
(a) a straight-chain or branched alkoxy radical having up to 6 carbon atoms, or a cycloalkoxy radical having up to 6 carbon atoms, or a straight-chain or branched alkenyloxy or alkynyloxy radical having 3 to 6 carbon atoms,
(b) cycloalkyl having 3-7 carbon atoms, an unsubstituted phenyl, α- or β-thienyl or α- or β-furyl radical, or a phenyl, thienyl or furyl radical which in turn is substituted in the nucleus once to 3 times by halogen, trifluoromethyl and/or alkyl or alkoxy having 1-6 carbon atoms,
(c) an unsubstituted phenoxy, α- or β-thienyloxy or cyclo-alkoxy radical having 3-7 carbon atoms, or one of the radicals mentioned which in turn is substituted in the nucleus once to 3 times by halogen, trifluoromethyl and/or alkyl or alkoxy each having 1-4 carbon atoms,
(d) a heteroaryl radical.

The following substituents are particularly preferred: $R^1$ and $R^2$ together with the carbon atom to which they are attached are the carbonyl group, or $R^1$ is hydrogen and $R^2$ is the radical $-OR^4$, in which $R^4$ represents hydrogen, benzyl, alkyl having 1-6 carbon atoms or the radical

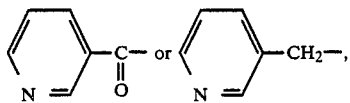

$R^3$ is a cycloaliphatic radical having 3-8 carbon atoms, a straight-chain or branched alkyl radical having up to 8 carbon atoms, a straight-chain or branched unsaturated aliphatic hydrocarbon radical having 3 to 8 carbon atoms, it being possible for the aliphatic radicals in turn to be substituted by
(a) a straight-chain or branched alkoxy radical having up to 10 carbon atoms,
(b) cycloalkyl having 3-7 carbon atoms, an unsubstituted phenyl, α- or β-thienyl or α- or β-furyl radical, or a phenyl, thienyl or furyl radical, which in turn is substituted in the nucleus once to 3 times by halogen, trifluoromethyl and/or alkyl or alkoxy having 1-6 carbon atoms,
(c) an unsubstituted phenoxy, α- or β-thienyloxy or cyclo-alkoxy radical having 3-7 carbon atoms,
(d) a 1-imidazolyl radical, in particular the following radicals: n-pentyl, 1,1-dimethylpentyl, cyclopentylmethyl, cyclohexylmethyl, methoxymethyl, ethoxymethyl, propoxymethyl, butoxymethyl, pentoxymethyl, hexyloxymethyl, heptyloxymethyl, cyclopentyloxymethyl, cyclohexyloxymethyl, dimethylpentoxymethyl, 1,1-dimethyl-2-ethoxyethyl, phenoxymethyl, 2-ethoxyethyl, 2-butoxyethyl, 3-ethoxypropyl, 5-methoxypentyl, (2-ethoxy)ethoxymethyl, 3-chlorophenoxymethyl, 1,1-dimethyl-2-benzyloxyethyl, 3-methoxycarbonylpropyl, 4-methoxycarbonylbutyl, 5-methoxycarbonylpentyl, 3-carboxypropyl, 4-carboxybutyl, 5-carboxypentyl, 4-(3-chlorobenzyloxy)phenyl, phenylethoxymethyl, 3-thienyloxymethyl, 2-thienyloxymethyl, 2-(1-imidazolyl)ethyl and dimethyl(1-imidazolyl).

The invention further relates to acid addition salts with inorganic or organic acids, for example hydrochloric acid, hydrobromic acid, sulfuric acid, phosphoric acid or nitric acid, acetic acid, propionic acid, oxalic acid, malonic acid, glycolic acid, succinic acid, maleic acid, fumaric acid, malic acid, tartaric acid, citric acid, benzoic acid or cinnamic acid.

The invention furthermore relates to a process for the preparation of the compounds of the general formula I, which comprises
(a) reacting the corresponding ortho-, meta- and para-substituted benzaldehydes of the formula II

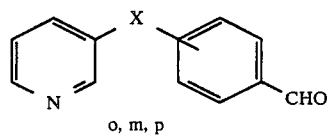

by the method of Horner-Emmons-Wittig with a phosphonic ester of the general formula III

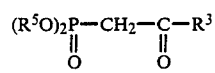

$R^3$ having the meaning indicated in the general formula I, and $R^5$ denoting $C_1$-$C_4$-alkyl, preferably methyl and ethyl, to give compounds of the general formula IV

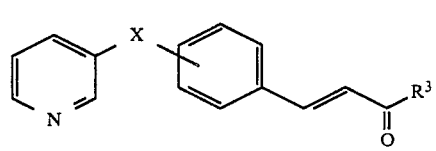

$R^3$ having the meaning indicated for formula I,
(b) where appropriate reducing the enones of the general formula IV with a reducing agent to give the alcohols of the general formula V

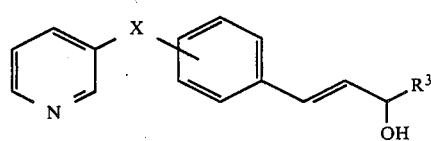

in which $R^3$ has the meaning given for formula I,
(c) where appropriate reacting the alcohols of the formula V in the form of their racemates, or as the pure enantiomers, with a reactive derivative of a carboxylic acid to give the esters of the general formula VI

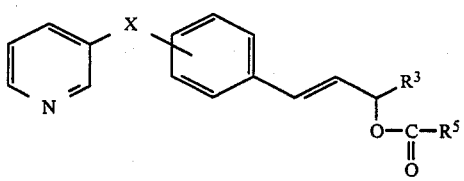

in which $R^3$ has the meaning indicated for formula I, and $R^4$ denotes a branched or unbranched aliphatic acyl radical having up to 10 carbon atoms, or the benzylcarbonyl or benzoyl radical, in which the phenyl nucleus can be substituted once to 3 times by halogen or $C_1$–$C_4$-alkyl, or denotes the radical

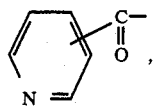

or (d) where appropriate reacting the alcohols of the formula V in the form of their racemates, or as the pure enantiomers, with an appropriate halide, tosylate or mesylate to give the ethers of the general formula VII

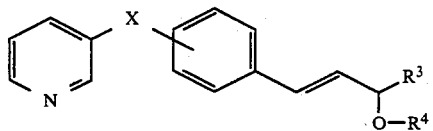

in which $R^4$ represents $C_1$–$C_{10}$-alkyl, benzyl, in which the phenyl nucleus can be substituted once to 3 times by halogen or $C_1$–$C_6$-alkyl, or represents the radical

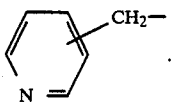

The preparation of the 2-(3-pyridyl)ethenylbenzaldehydes which are used as starting materials in the process according to the invention starts from the corresponding o-, m- and p-chloromethylbenzaldehydes. The chloromethylbenzaldehydes can be prepared in analogy to known processes (for example R. Grice, L. N. Owen, J. Chem. Soc. 1963, 1947 or I. W. Baker, I. A. L. Brieux, D. G. Saunders, J. Chem. Soc. 1956, 404).

The ethylene acetals of the latter aldehydes are converted in a known manner (B. A. Arbuzov, Pure Appl. Chem. 9, 307 (1964)) using triethyl phosphite into the corresponding phosphonates. These in turn are reacted in a known manner (W. S. Wadsworth et al., J. Am. Chem. Soc. 83, 1733 (1961), J. Org. Chem. 30, 680 (1965)) with pyridine-3-aldehyde to give the ethylene acetals of the corresponding o-, m- and p-[2-(3-pyridyl-)ethenyl]benzaldehydes. The latter can be catalytically hydrogenated to give the o-, m- and p-[2-(3-pyridyl)ethyl]benzaldehyde ethylene acetals respectively.

The o-, m- and p-substituted benzaldehydes of the formula II are reacted by the method of Horner-Emmons-Wittig with a phosphonic ester of the general formula III, a preferred embodiment of this comprising reaction of the phosphonic esters of the formula III with the aldehyde of the formula II in dimethoxyethane using DBU (1,8-diazabicyclo[5.4.0]undec-7-ene) as the base at room temperature up to the reflux temperature for 1–36 hours.

The phosphonic esters of the formula III can be prepared by methods known from the literature (see, for example, J. Am. Chem. Soc. 88, 5654 (1966)).

The alcohols of the general formula V are obtained in the form of their racemates when an enone of the general formula IV is reduced with a complex metal hydride, preferably with an alkali metal boranate, preferably between $-10°$ C. and room temperature, in methanol, ethanol or ethers such as DME or THF, where appropriate with the addition of water.

The acylation of the alcohols of the formula V to give the esters of the formula VI is carried out in the generally customary manner using acyl halides (such as, for example, nicotinoyl chloride) or acid anhydrides in the presence of bases such as pyridine, triethylamine, inter alia.

The etherification of the alcohols of the formula V to give the ethers of the formula VII is carried out in the generally customary manner using halides (such as, for example, benzyl halide), mesylates or tosylates in the presence of bases such as, for example, sodium hydride, in suitable solvents such as, for example, DMF.

Where the individual reaction products do not result in a form which is already sufficiently pure for it to be possible for them to be used for the subsequent reaction step, it is advisable to carry out a purification by crystallization or column, thin-layer or high-pressure liquid chromatography.

The acid addition salts of compounds of the general formula I are obtained by addition of the appropriate inorganic or organic acids, usually in the form of a solution, to solutions of the appropriate pyridyl compound of the general formula 1. Examples of solvents which are used are water and alcohols as well as various ethers and esters.

Apart from the compounds described in the examples, the following compounds can be prepared by the process according to the invention: E,E-4-ethoxy-1-[4-(2-(3-pyridyl)ethenyl)phenyl]but-1-en-3-ol, E,E-5-ethoxy-1-[4-(2-(3-pyridyl)ethenyl)phenyl]pent-1-en-3-ol, E,E-5-butoxy-1-[4-(2-(3-pyridyl)ethenyl)phenyl]pent-1-en-3-ol, E,E-4-ethoxy-1-[4-(2-(3-pyridyl)ethenyl)phenyl]but-1-en-3-one, E,E-5-ethoxy-1-[4-(2-(3-pyridyl)ethenyl)phenyl]pent-1-en-3-one, E,E-5-butoxy-1-[4-(2-(3-pyridyl)ethenyl)phenyl]pent-1-en-3-one, E,E-6-ethoxy-1-[4-(2-(3-pyridyl)ethenyl)phenyl]hex-1-en-3-one, E,E-6-ethoxy-1-[4-(2-(3-pyridyl)ethenyl)phenyl]hex-1-en-3-ol, E,E-7-methoxy-1-[4-(2-(3-pyridyl)ethenyl)phenyl]hept-1-en-3-one, E,E-7-methoxy-1-[4-(2-(3-pyridyl)ethenyl)phenyl]hept-1-en-3-ol, E,E-8-methoxy-1-[4-(2-(3-pyridyl)ethenyl)phenyl]oct-1-en-3-one, E,E-8-methoxy-1-[4-(2-(3-pyridyl)ethenyl)phenyl]oct-1-en-3-ol, E,E-5-(1-imidazolyl)-1-[4-(2-(3-pyridyl)ethenyl)phenyl]pent-1-en-3-ol, E,E-4,4-dimethyl-4-(1-imidazolyl-1-[4-(2-(3-pyridyl)ethenyl)phenyl]but-1-en-3-one, E,E-4,4-dimethyl-4-(1-imidazolyl-1-[4-(2-(3-pyridyl)ethenyl)phenyl]but-1-en-3-ol, E,E-3-(3-chlorophenyl)-1-[4-(2-(3-pyridyl)ethenyl)phenyl]prop-1-en-3-one, E,E-3-(3-chlorophenyl)-1-[4-(2-(3-pyridyl- )ethenyl)phenyl]prop-1-en-3-ol, E,E-4-ethoxy-1-[4-(2-(3-pyridyl)ethyl)phenyl]but-1-en-3-ol, E,E-5-ethoxy-1-[4-(2-(3-pyridyl)ethyl)phenyl]pent-1-en-3-ol, E,E-5-butoxy-1-[4-(2-(3-pyridyl)ethyl)phenyl]pent-1-en-3-ol, E,E-4-ethoxy-1-[4-(2-(3-pyridyl)ethyl)phenyl]but-1-en-3-one, E,E-5-ethoxy-1-[4-(2-(3-pyridyl)ethyl)phenyl]pent-1-en-3-one, E,E-5-butoxy-1-[4-(2-(3-pyridyl)ethyl)phenyl]pent-1-en-3-one, E,E-6-ethoxy-1-[4-(2-(3-pyridyl)ethyl)phenyl]hex-1-en-3-one, E,E-6-ethoxy-1-[4-(2-(3-pyridyl)ethyl)phenyl]hex-1-en-3-ol, E,E-7-methoxy-1-[4-(2-(3-pyridyl)ethyl)phenyl]hept-1-en-3-one, E,E-7-methoxy-1-[4-(2-(3-pyridyl)ethyl)phenyl]hept-1-en-3-ol, E,E-8-methoxy-1-[4-(2-(3-pyridyl)ethyl)phenyl]oct-1-en-3-one, E,E-8-methoxy-1-[4-(2-(3-pyridyl)ethyl)phenyl]oct-1-en-3-ol, E,E-5-(1-imidazolyl)-1-[4-(2-(3-pyridyl)ethyl)phenyl]pent-1-en-3-ol, E,E-4,4-dimethyl-4-(1-imidazolyl-1-[4-(2-(3-pyridyl)ethyl)phenyl]but-1-en-3-one, E,E-4,4-dimethyl-4-(1-imidazolyl-1-[4-(2-(3-pyridyl)ethyl)phenyl]but-1-en-3-ol, E,E-3-(3-chlorophenyl)-1-[4-(2-(3-pyridyl)ethyl)phenyl]prop-1-en-3-one and E,E-3-(3-chlorophenyl)-1-[4-(2-(3-pyridyl)ethyl)phenyl]prop-1-en-3-ol, and the nicotinic esters, benzyl ethers and (3-pyridyl)-methyl ethers of the alcohols listed here and in Table 2.

The compounds of the formula I are distinguished by having a specific inhibitory effect on thromboxane synthetase and can thus be used as medicaments for the prophylaxis or treatment of disorders where there is a disturbance (an increase) of the tendency of platelets to aggregate, and where there are pathologically raised levels of thromboxane, as are found with ischemia, angina pectoris, thromboembolic diseases, atherosclerosis, coronary spasms, arrhythmias, cerebral ischemic attacks, migraine and other vascular headaches, myocardial infarct, hypertension, breathing disturbances such as asthma and apnea, inflammatory disorders, and microvascular complications of diabetes mellitus. The compounds according to the invention have favorable effects on diseases where there are raised levels of thromboxane in various organs, for example in the region of the kidneys or in the gastrointestinal region associated with colitis or inflammatory bowel disease.

Some of the compounds according to the invention additionally have pronounced hypolipidemic actions with preferential reduction of the atherogenic LDL and VLDL lipoprotein fractions. Hence they are suitable as lipid-lowering agents and for the treatment of arteriosclerosis. The compounds are active in doses of from 0.01 mg/kg to 10 mg/kg. The individual dose which is administered can be between 1 mg and 500 mg, and the preferred daily dose is between 1 mg and 1 g on oral administration.

Metabolites of arachidonic acid are involved in a large number of physiological and pathophysiological processes. Prostacyclin (PGI$_2$) and thromboxane A$_2$ (TXA$_2$) play an essential part in the regulation of blood vessel tone and of blood platelet aggregation. Prostacyclin, which is produced from prostaglandin endoperoxide H$_2$ (PGH$_2$) preferentially in the endothelial cells of the blood vessels, brings about vasodilatation and prevents the aggregation of blood platelets. The conversion of prostaglandin endoperoxide into prostacyclin is catalyzed by the enzyme prostacyclin synthetase. Thromboxane A$_2$ is the physiological antagonist of prostacyclin. It is produced from PGH$_2$, mainly in the blood platelets. The enzymes thromboxane synthetase catalyzes this reaction. TXA$_2$ brings about aggregation of blood platelets and leads to vasoconstriction. As far as is known, thromboxane is the most potent vasoconstrictor in the human body (A. G. Hermann, P. M. Vonhoutte, H. Denolin, A. Goossens, Cardiovascular Pharmacology of the Prostaglandins, Raven Press, New York 1982). Imbalances between prostacyclin and thromboxane A$_2$ lead to pathophysiological situations. A shift in the equilibrium in favor of thromboxane thus leads to platelet aggregation and vasospasms and to an increased susceptibility to atherothrombosis (Lancet 1977, 479; Science 1976, 1135; Amer. J. Cardiology 41, 787 (1978); Lancet 1977, 1216). In experimental atherosclerosis, the formation of PGI$_2$ is suppressed and the formation of TXA$_2$ is raised (Prostaglandins 14, 1025 and 1035 (1977)). For this reason, thromboxane A$_2$ has been connected with various types of angina, formation of myocardial infarcts, sudden heart death and strokes (Thromb. Haemostasis 38, 132 (1977); Platelets, Prostaglandins and Cardiovascular System, Florence, February 1984).

Another area in which an imbalance of PGI$_2$ and TXA$_2$ is regarded as a contributory factor is that of migraine. Migrainous headache is connected with changes in the intra- and extra-cerebral blood flow, in particular with a reduction, which takes place before the occurrence of the headache, in the cerebral blood flow and subsequent dilatation in both vascular regions during the headache phase. Blood platelets from migraine patients have a greater tendency to aggregation than do those from normal individuals (J. clin. Pathol. 24, 250 (1971); J. Headache, 17, 101 (1977); Lancet 1978, 501).

In patients with diabetes mellitus, an imbalance between prostacyclin and thromboxane A$_2$ is regarded as being responsible for the microvascular complications. Platelets from diabetic patients form increased amounts of TXB$_2$ and malondialdehyde, see the symposium "Diabetes and Thrombosis—Implications for Therapy", Leeds, Great Britain (April 1979). Furthermore, it has been shown that the vascular formation of prostacyclin is inhibited in rats with experimentally induced diabetes, and the TXA$_2$ synthesis from the platelets is raised, see Ivth International Prostaglandin Conference, Washington, D.C. (May 1979).

Non-steroidal antiinflammatory agents inhibit cyclooxygenase, which catalyzes the conversion of arachidonic acid into PGH$_2$ via PGG$_2$. Thus, they intervene not only in the biosynthesis of thromboxane but also in the biosynthesis of prostacyclin. Thus, a compound which specifically inhibits the formation of TXA$_2$ by blockade of TXA$_2$ synthetase and leaves the prostacyclin route unaffected would be more valuable.

Thus the compounds of the formula I are suitable for the prophylaxis or treatment of the abovementioned diseases which respond to inhibition of thromboxane synthetase.

The compounds of the formula I are administered in various dosage forms, for example orally in the form of tablets, capsules or liquids, rectally in the form of suppositories, parenterally, subcutaneously or intramuscularly, and intravenous administration is preferred in emergency situations.

The compounds according to the invention, of the formula I, can be used as free bases or in the form of their physiologically acceptable inorganic or organic acid addition salts. The free bases and acid addition salts can be used in the form of their aqueous solutions or suspensions as well as dissolved or suspended in pharmacologically acceptable organic solvents, such as monohydric or polyhydric alcohols such as, for example, ethanol, ethylene glycol or glycerol, in triacetin, in alcohol/acetaldehyde diacetal mixtures, oils such as, for example, sunflower oil or fish liver oil, ethers such as, for example, diethylene glycol dimethyl ether, as well as polyethers such as, for example, polyethylene glycol, as well as in the presence of other pharmacologically acceptable polymeric vehicles such as, for example, polyvinylpyrrolidone.

Suitable possible formulations are the customary pharmaceutical solutions for infusion or injection, and tablets, as well as formulations which can be applied topically, such as creams, emulsions, suppositories or aerosols.

EXAMPLE 1A

E-4-[2-(3-Pyridyl)ethenyl]benzaldehyde ethylene acetal 10.11 g (50.9 mmol) of 4-chloromethylbenzaldehyde ethylene acetal and 8.46 g (50.9 mmol) of triethyl phosphite were heated without solvent, with magnetic stirring, at an oil bath temperature of 200°–210° C. until gas evolution was complete (about 1 h). After cooling, 70 ml of dimethylformamide (filtered through basic alumina, activity I) and 5.5 g (102.0 mmol) of sodium methylate were added. The mixture was cooled to 5° C. and, with magnetic stirring and cooling, a solution of 5.45 g (50.9 mmol) of pyridine-3-aldehyde in 20 ml of dimethylformamide was added dropwise within 15 min (during which the temperature rose to 25° C.), and the mixture was then stirred at room temperature for 1 h. The reaction mixture was diluted with 250 ml of toluene and washed twice with water. The combined wash phases were extracted twice with toluene. Drying of the combined organic phases over magnesium sulfate and removal of the solvent in vacuo provided 10.94 g of a yellowish solid. Recrystallization from cyclohexane produced 8.74 g, and working up of the mother liquor produced a further 0.60 g.

Yield 9.34 g (36.9 mmol, 72%).
Melting point: 117°–119° C.
$^1$H NMR (60 MHz, CDCl$_3$): $\delta$=4.0 (m, 4H, methylene-H), 5.8 (s, 1H, methyne-H), 7.0–8.8 (m, 10H olefinic and aromatic H).

EXAMPLE 1B

E-2-[2-(3-Pyridyl)ethenyl]benzaldehyde ethylene acetal is obtained in analogy to 1a.

$^1$H NMR (60 MHz, CDCl$_3$) $\delta$=4.2 (m, 4H, methylene-H), 5.8 (s, 1H, methyne-H), 7.0–8.9 (m, 10H, olefinic and aromatic H).

EXAMPLE 1C

E-3-[2-(3-Pyridyl)ethenyl]benzaldehyde ethylene acetal is obtained in analogy to 1a:

$^1$H NMR (60 MHz, CDCl$_3$): $\delta$=4.1 (m, 4H, methylene-H), 5.9 (s, 1H, methyne-H), 7.1–8.9 (m, 10H, olefinic and aromatic H).

EXAMPLE 2A

E-4-[2-(3-Pyridyl)ethyl]benzaldehyde 8.56 g (33.8 mmol) of acetal 1a were dissolved in 80 ml of 1N aqueous hydrochloric acid, and the solution was stirred at room temperature for 3.5 h. Then the solution was cautiously poured, while stirring, into 100 ml of saturated aqueous sodium bicarbonate solution. In order to dissolve the precipitated product, about 100 ml of toluene were added and the mixture was stirred vigorously at room temperature. The phases were separated, and the aqueous phase was saturated with sodium chloride and extracted twice with toluene. Drying of the combined organic phases over magnesium sulfate, removal of the solvent in a rotary evaporator and finally at the oil pump produced 6.96 g (33.3 mmol, 98%) of aldehyde 2a as a yellow solid.

Melting point 69°–73° C.
IR (KBr): 1690 cm$^{-1}$ (s, carbonyl).
$^1$H NMR (CDCl$_3$, 60 MHz): $\delta$=7.0–8.8 (m, 10H, olefinic and aromatic H), 10.0 (s, 1H, —CHO).

EXAMPLE 2B

E-2-[2-(3-Pyridyl)ethenyl]benzaldehyde is obtained in analogy to 2a

NMR: (CDCl$_3$) $\delta$ values: 60 MHz spectrum 6.9–8.9 (m, 10H, aromatic+olefinic protons) 10.3 (s, 1H, C$\underline{H}$=0).

EXAMPLE 2C

E-3-[2-(3-Pyridyl)ethenyl]benzaldehyde is obtained in analogy to 2a.

IR (KBr): 1690 cm$^{-1}$ (s, carbonyl).
$^1$H NMR (60 MHz, CDCl$_3$): $\delta$=6.9–8.8 (m, 10H, olefinic and aromatic H), 9.9 (s, 1H, —CHO).

EXAMPLE 3A

4-[2-(3-Pyridyl)ethyl]benzaldehyde ethylene acetal 10 g (39.5 mmol) of E-4-[2-(3-pyridyl)ethenyl]benzaldehyde ethylene acetal (1a) were dissolved in 100 ml of ethanol, 1.6 g of palladium on charcoal (10%) were added, and hydrogenation was carried out at room temperature and under atmospheric pressure. Filtration and removal of the solvent in vacuo produced 8.6 g (33.7 mmol, 85%) of a white solid.

Melting point: 46°–47° C.
$^1$H NMR (60 MHz, CDCl$_3$): $\delta$=2.8 (m, 4H, —CH$_2$CH$_2$—), 3.9 (m, 4H, acetal methylene H), 5.6 (s, 1H, methyne H), 7.0–8.2 (m, 8H, aromatic H).

EXAMPLE 3B:

2-[2-(3-Pyridyl)ethyl]benzaldehyde ethylene acetal is obtained in analogy to 3a.

$^1$H NMR (60 MHz, CDCl$_3$): $\delta$=2.7 (m, 4H, CH$_2$CH$_2$), 3.8 (m, 4H, acetal methylene H), 5.7 (s, 1H, methyne H), 7.1–8.3 (m, 8H, aromatic H).

EXAMPLE 3C:

3-[2-(3-Pyridyl)ethyl]benzaldehyde ethylene acetal is obtained in analogy to 3a $^1$H NMR (60 MHz, CDCl$_3$): $\delta$=2.8 (m, 4H, —CH$_2$CH$_2$—), 3.9 (m, 4H, acetal methylene H), 5.8 (s, 1H, methyne H), 7.0–8.2 (m, 8H, aromatic H).

EXAMPLE 4A:

4-[2-(3-Pyridyl)ethyl]benzaldehyde 8.5 g (33.7 mmol) of acetal 3a were dissolved in 85 ml of 1N hydrochloric acid and stirred at room temperature for 3.5 h. The solution was neutralized with 80 ml of saturated sodium bicarbonate solution and extracted three times with toluene. Drying of the combined toluene phases with magnesium sulfate and removal of the solvent in vacuo produced 6.1 g (28.9 mmol, 86%) of aldehyde 4a as a yellowish oil.

IR (film): 1690 cm$^{-1}$ (s, carbonyl).

$^1$H NMR (60 MHz, CDCl$_3$): δ=2.9 ("s", 4H, —CH$_2$CH$_2$—), 6.9-8.4 (m, 8H, aromatic H), 9.7 (s, 1H, —CHO).

EXAMPLE 4B:

2-[2-(3-Pyridyl)ethyl]benzaldehyde is obtained in analogy to 4a.

IR (film): 1690 cm$^{-1}$ (s, carbonyl).

$^1$H NMR (60 MHz, CDCl$_3$): δ=2.8 ("s", 4H, —CH$_2$CH$_2$—), 7.0-8.3 (m, 8H, aromatic H), 9.8 (s, 1H, —CHO).

EXAMPLE 4C:

3-[2-(3-Pyridyl)ethyl]benzaldehyde is obtained in analogy to 4a.

IR (film): 1690 cm$^{-1}$ (s, carbonyl).

$^1$H NMR (60 MHz, CDCl$_3$): δ=2.9 (m, 4H, —CH$_2$CH$_2$—), 7.0-8.4 (m, 8H, aromatic H), 9.9 (s, 1H, —CHO).

EXAMPLE 5:

Dimethyl 2-oxo-3-pentyloxypropanephosphonate 25.6 g (0.2 mole) of dimethyl methanephosphonate were initially introduced into 200 ml of dry tetrahydrofuran under an argon atmosphere. 250 ml of a 1.6 molar solution of butyllithium (0.4 mole) in hexane and 100 ml of a solution of 32.04 g (0.2 mole) of methyl 2-pentyloxyacetate in tetrahydrofuran were initially introduced into two separate dropping funnels. Then, at −70° C. to −65° C., 125 ml of the butyllithium solution and, immediately thereafter, 50 ml of the ester solution were added dropwise. The mixture was stirred at −70° C. for 1 h, and then a further 63 ml of the butyllithium solution and 25 ml of the ester solution were added at −70° C., and the mixture was stirred at this temperature for 1 h. Finally, the remaining 62 ml of the butyllithium solution and 25 ml of the ester solution were added dropwise at the same temperature, and the mixture was stirred for 2 h. It was allowed to stand in dry ice overnight.

For working up, the pH of the solution was adjusted to 5 and 0°-5° C. with about 160 ml of 2N aqueous hydrochloric acid, and then the THF was removed in a rotary evaporator. The residue was taken up in saturated aqueous sodium chloride solution, and the solution was extracted four times with ethyl acetate. Drying of the combined ethyl acetate phases over magnesium sulfate, removal of the solvent in vacuo, and fractional distillation produced 37.0 g (0.147 mole, 73%) of phosphonate as a colorless liquid, boiling point 130°-132° C./0.5 torr.

IR (film): 1730 cm$^{-1}$ (s, carbonyl).

$^1$H NMR (60 MHz, CDCl$_3$): δ=0.8-1.8 (m, 9H, —(CH$_2$)$_3$CH$_3$), 3.16 (d, J=22 Hz, 2H, P—CH$_2$—), 3.47 (t, J=6 Hz, 2H, —OCH$_2$—), 3.75 (d, J=11 Hz, 6H, —OCH$_3$), 4.1 (s, 2H, —CH$_2$—).

The phosphonates of the formula III are obtained in analogy to Example 5. The esters used as starting material are substantially known from the literature or are prepared in analogy to known processes.

EXAMPLE 6A:

E,E-4-Pentyloxy-1-[4-(2-(3-pyridyl)ethenyl)phenyl]but-1-en-3-one 1.57 g (6.21 mmol) of dimethyl 2-oxo-3-pentyloxypropanephosphonate, 1.0 g (6.54 mmol) of DBU and 1.3 g (6.21 mmol) of 4-[2-(3-pyridyl)ethenyl]benzaldehyde (2a) in 150 ml of dimethoxyethane were stirred at room temperature for 22 h. The solvent was removed in vacuo, and the residue was chromatographed on 200 g of silica gel (petroleum ether/ethyl acetate=1:1, Rf=0.38). After crystallization from ether/n-hexane, 1.4 g (4.17 mmol, 67%) of enone 6a was obtained.

Melting point: 78°-80° C.

IR (KBr): 1700 cm$^{-1}$ (carbonyl).

$^1$H NMR (60 MHz, CDCl$_3$): δ=0.6-2.0 (m, 9H, (CH$_2$)$_3$CH$_3$), 3.5 (t, 2H, OCH$_2$—), 4.25 (s, 2H, OCCH$_2$O), 6.90-8.75 (m, 12H, olefinic acid aromatic H).

Other compounds, inter alia the Examples 6b-6t listed in Table 1, are obtained in analogy to Example 6a.

TABLE 1

| Example | R | characteristic $^1$H NMR signals (CDCl$_3$, 60 MHz), δ | Rf, silica gel |
|---|---|---|---|
| X = —CH=CH—, E | | | |
| 6b | (structure: para-substituted with enone and pentyloxy chain) | 0.6-2.0 (m, 15H methyl and CH$_2$)$_3$CH$_3$) | 0.5 ethyl acetate |
| 6c | (structure: para-substituted with enone and phenoxy) | 4.8 (s, 2H, —CH$_2$OPh) | 0.4 ethyl acetate |

TABLE 1-continued

| Example | R | characteristic $^1$H NMR signals (CDCl$_3$, 60 MHz), δ | Rf, silica gel |
|---|---|---|---|
| 6d | (structure: CH$_3$-CH=CH-CH$_2$-C(O)-C(CH$_3$)$_2$-CH$_2$-O-CH$_2$-C$_6$H$_5$) para | m.p. 80–82° C. 1.2 (s, 6H, CH$_3$); 3.5 (s, 2H, CH$_2$O), 4.5 (s, 2H, CH$_2$OC$_6$H$_5$) 7.1–8.65 (m, 17H, aromat. olefin.protons) | 0.38 CH$_2$Cl$_2$/MeOH=20:1 |
| 6e | (structure: CH$_3$-CH=CH-CH$_2$-C(O)-(CH$_2$)$_3$-C(O)-OCH$_3$) para | m.p. 118–120° C. 1.9–2.9 (m, 6H, CH$_2$), 3.7 (s, 3H, COOCH$_3$); 6.6–8.9 (m, 12H, aromat. olefin.protons) | 0.59 CH$_2$Cl$_2$/MeOH=10:1 |
| 6f | (structure: CH$_3$-CH=CH-CH$_2$-C(O)-C(CH$_3$)$_2$-CH$_2$-O-CH$_2$CH$_3$) para | 1.17 (t, 3H, —CH$_2$—CH$_3$); 1.25 (s, 6H, H$_3$CCCH$_3$), 3.5 (q and t, 4H, methylene H) | 0.41 ethyl acetate |
| 6g | (structure: CH$_3$-CH=CH-CH$_2$-C(O)-CH$_2$CH$_2$-furan) para | 3.0 ("s", 4H, methylene H) | 0.35 EA/n-hexane=7:3 |
| 6h | (structure: CH$_3$-CH=C(CH$_3$)-C(O)-(CH$_2$)$_4$-CH$_3$) para | m.p. 110–112° C.; 0.9 (t, 3H, CH$_3$) 1.1–1.9 (m, 6H, CH$_2$); 2.1 (d, 3H, CH$_3$); 2.65–2.95 (m, 2H, CH$_2$CO) 7.1–8.9 (m, 11H, aromat., olefin. protons) | 0.37 CH$_2$Cl$_2$/MeOH=20:1 |
| 6i | (structure: CH$_3$-CH=CH-CH$_2$-C(O)-CH$_2$-O-(2-chlorothiophen-3-yl)) para | m.p. 113° C. 4.85 (s, 2H, CH$_2$O), 6.6–8.9 (m, 14H, aromat. olefin.protons) | 0.6 CH$_2$Cl$_2$/MeOH=10:1 |
| 6j | (structure: CH$_3$-CH=CH-C(O)-C$_6$H$_4$-O-CH$_2$-(3-chlorophenyl)) Para | 5.1 (s, 2H, CH$_2$O) 7.0–8.8 (m, 20H, aromat., olefin. protons) | 0.62 CH$_2$Cl$_2$/MeOH=10:1 |
| 6k | (structure: CH$_3$-CH=CH-CH$_2$-C(O)-CH(OCH$_2$CH$_3$)-C$_6$H$_5$) para | 1.4 (t, 3H, CH$_3$), 3.6 (q, 2H, CH$_2$O), 4.95 (s, 1H, CHO), 7.0–8.8 (m, 17H, aromat., olefin. protons | 0.45 ethyl acetate/MeOH=8:2 |

TABLE 1-continued

| Example | R | characteristic ¹H NMR signals (CDCl₃, 60 MHz), δ | Rf, silica gel |
|---|---|---|---|
| 6l | 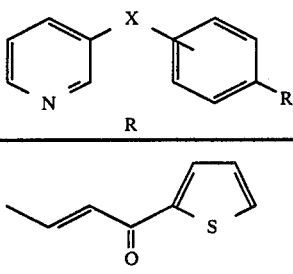 para | 6.5–8.8 (m, 15H, aromat., olefin. protons) | 0.43 ethyl acetate/ MeOH=8:2 |
| 6m | 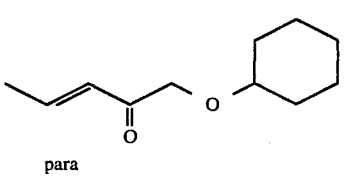 para | 1,0–2,2 (m, 10H, methylene H), 3,33 (m, 1H, methyne H), 4,23 (s, 2H, —OCH₂—) | 0.48 ethyl acetate |
| 6n | 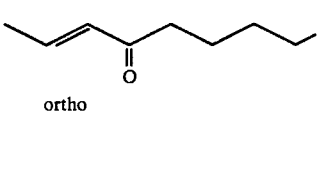 ortho | 0.9 (t, 3H, CH₃), 1.0–2.0 (m, 6H, CH₂), 2.6 (t, 2H, C$\underline{\text{H}}$₂CO), 6.5–8.8 (m, 12H, aromat. olefin. protons) | Rf=0.42 cyclohexane/ ethyl acetate=1:1 |
| 6o | 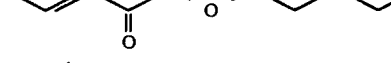 ortho | 0.8–2.1 (m, 9H, Alkyl H), 3.5 (t, 2H, —OCH₂—) 4.2 (s, 2H, —OCCH₂O—) | 0.35 EA/n-hexane=2:1 |
| 6p | 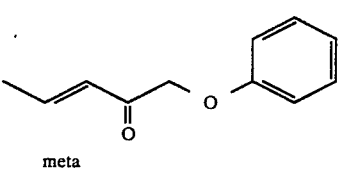 meta | 4,9 (s, 2H, —C$\underline{\text{H}}$₂OPh) | 0.45 ethyl acetate |

X = —CH₂—CH₂—

| 6q | 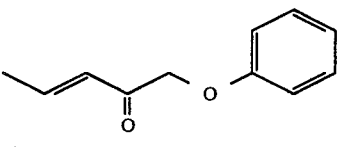 para | 2.96 ("s", 4H, —CH₂CH₂—), 4,76 (s, 2H, —CH₂OPh) | 0.37 ethyl acetate |
| 6r | 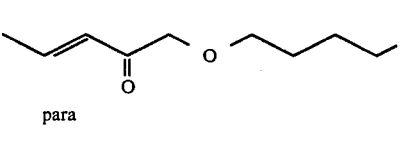 para | 0,6–2,0 (m, 9H, alkyl H), 2.96 ("s", 4H, —CH₂CH₂—) 3.5 (t, 2H, OCH₂—), 4.23 (s, 2H, OCCH₂O) | 0.46 ethyl acetate/ n-hexane=7:3 |
| 6s | 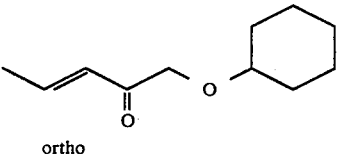 ortho | 0,9–2,2 (m, 10H, methylene H), 3.0 ("s", 4H, —CH₂CH₂—), 3,3 (m, 1H, methyne H), 4,21 (s, 2H, —OCH₂—) | 0.41 ethyl acetate/ n-hexane=7:3 |
| 6t | 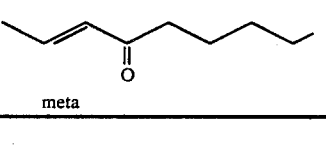 meta | 0.6–2.0 (m, 9H, (CH₂)₃CH₃), 2,65 (t, 2H, —COCH₂—) 3.0 ("s", 4H, —CH₂CH₂—) | 0.38 ethyl acetate/ cyclohexane=1:1 |

EXAMPLE 7A

E,E-4-Phenoxy-1-[4-(2-(3-pyridyl)ethenyl)phenyl]but-1-en-3-ol 0.3 g (7.93 mmol) of sodium boranate was initially introduced into 20 ml of methanol and 4 ml of tetrahydrofuran at $-5°$ C. At $-5°$ C., 0.8 g (2.51 mmol) of enone 6c in 10 ml of methanol and 4 ml of tetrahydrofuran was added dropwise. The mixture was stirred at this temperature for 60 min, acidified with an aqueous solution of citric acid, and the solvent was substantially removed in vacuo. The residue was partitioned between saturated sodium bicarbonate solution and methylene chloride. The aqueous phase was extracted twice with methylene chloride. Drying of the organic phases with magnesium sulfate and removal of the solvent in vacuo produced after chromatography on silica gel ($CH_2Cl_2/CH_3OH=9:1$) 0.78 g (2.27 mmol, 90%) of alcohol 7a.

Melting point: 106°–108° C.

IR (KBr): 3250 cm$^{-1}$ (s, OH).

$^1$H NMR: (60 MHz, CDCl$_3$): $\delta=2.83$ (broad, 1H, OH), 4.08 (m, 2H, methylene H), 4.73 (m, 1H, methyne H), 6.0–8.7 (m, 17H, olefinic and aromatic H).

Other compounds, inter alia Examples 7b–7h listed in Table 2, are obtained in analogy to Example 7a.

TABLE 2

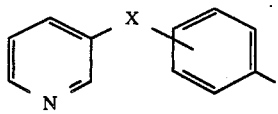

| Example | R | characteristic $^1$H NMR Signals (CDCl$_3$, 60 MHz), $\delta$ | Rf, silica gel |
|---|---|---|---|
| X = —CH=CH—, E | | | |
| 7b | 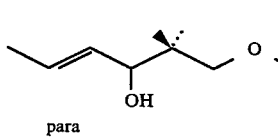 para | m.p. 114° C. 1.0 (d, 6H, CH$_3$), 3.2–3.6 (m, 2H, C$\underline{H}_2$O), 4.55 (s, 2H, CH$_2$OC$_6$H$_5$), 6.0–6.8 (m, 2H, CH=CH), 7.1–8.9 (m, 13H, aromat., olefin. protons) | 0.5 CH$_2$Cl$_2$/MeOH=20:1 |
| 7c | 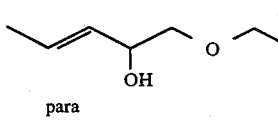 para | 0.65–2.0 (m, 9H, (CH$_2$)$_3$CH$_3$), 3.30–3.81 (m, 4H, —CH$_2$OCH$_2$—), 4.31–4.59 (m, 1H, methyne H) | 0.33 ethyl acetate/ cyclohexane=2:1 |
| 7d | 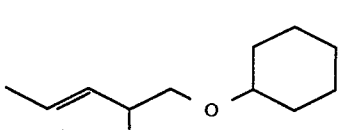 ortho | 1,01–2,32 (m, 10H, Methylene H), 4,5 (m, 1H, methyne H) | 0.48 ethyl acetate |
| 7e | 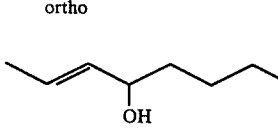 ortho | 0.9 (t, 3H, CH$_3$), 1.0–2.0 (m, 6H, CH$_2$), 4.1–4.5 (m, 1H, C$\underline{H}$OH), 5.9–6.9 (m, 2H, C$\overline{H}$=CH), 7.0–8.8 (m, 10H, aromat., olefin. protons) | 0.24 cyclohexane ethyl acetate=1:1 |
| X = —CH$_2$—CH$_2$— | | | |
| 7f | 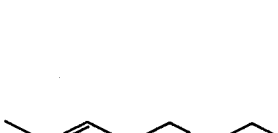 para | 0,66–1,83 (m, 9H, (CH$_2$)$_3$CH$_3$), 2,90 ("s", 4H, —CH$_2$CH$_2$—), 3,5 (m, 4H, —CH$_2$OCH$_2$—), 4,5 (m, 2H, methyne H) | 0,34 ethyl acetate/ n-hexane=7:3 |
| 7g | 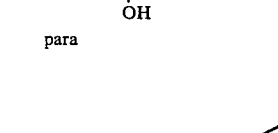 ortho | 1,0–2,3 (m, 10H, methylene H), 2,92 ("s", 4H, —CH$_2$CH$_2$—), 3,3 (m, 1H, methyne H), 4,5 (m, 1H, methyne H) | 0.32 ethyl acetate/ n-hexane 7:3 |

TABLE 2-continued

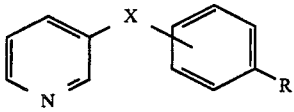

| Example | R | characteristic $^1$H NMR Signals (CDCl$_3$, 60 MHz), δ | Rf, silica gel |
|---|---|---|---|
| 7h | 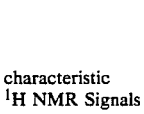<br>meta | 1,23 (t, 3H, —CH$_3$), 2,92 ("s", 4H, —CH$_2$CH$_2$—), 3,16–4,0 (m, 4H, —CH$_2$OCH$_2$—) 4,5 (m, 1H, methyne H) | 0,38 ethyl acetate |

EXAMPLE 8A

E,E-4-Phenoxy-3-(3-pyridylcarbonyloxy)-1-[4-(2-(3-pyridyl)ethenyl)phenyl]but-1-en-3-ol 440 mg (1.30 mmol) of alcohol 7a and 550 mg (3.1 mmol) of 3-pyridinecarbonyl chloride hydrochloride in 15 ml of pyridine and 15 ml of methylene chloride were stirred at room temperature overnight and then heated under reflux for 8 h. The mixture was poured onto saturated sodium bicarbonate solution. This mixture was extracted three times with methylene chloride, and the combined phases were dried with magnesium sulfate. Removal of the solvent in vacuo and chromatography on silica gel (ethyl acetate, Rf=0.19) produced 470 mg (1.04 mmol, 80%) as a yellowish oil.

IR (film): 1720 cm$^{-1}$ (ester carbonyl).

$^1$H NMR (60 MHz, CDCl$_3$): δ=4.4 (d, 2H, methylene H), 6.0–9.3 (m, 22H, methyne H, olefinic and aromatic H).

Further compounds, inter alia Examples 8b–d listed in Table 3, are obtained in analogy to Example 8a.

TABLE 3

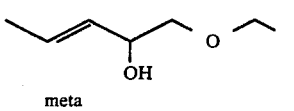

| Example | R | characteristic $^1$H NMR signals (CDCl$_3$, 60 MHz), δ | Rf silica gel |
|---|---|---|---|
| | | X = —CH=CH—, E | |
| 8b | 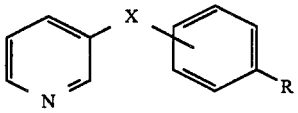<br>ortho | 0.9(t,3H,CH$_3$), 1.0–2.0(m,8H,CH$_2$), 4.9–5.4(m,1H,CHOCO—), 5.6–9.4(m,16H,aromat., olefin. protons) | 0.17 cyclohexane/ethyl acetate 1:1 |
| 8c | 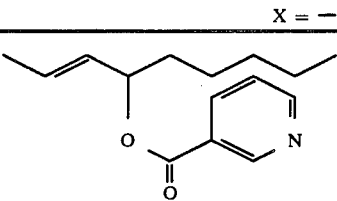<br>para | 1.0–2.3(m,10H,methylene H), 3.77(d,2H,—CH$_2$O—)6.0–9.3 (m,17H,methyne, olefin, and aromatic H) | 0.20 ethyl acetate |
| | | X = —CH$_2$—CH$_2$— | |
| 8d | 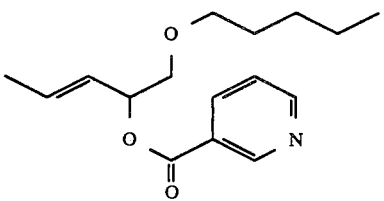<br>meta | 0.7–1.8(m,9H(CH$_2$)$_3$CH$_3$),3.0 ("s",4H,—CH$_2$CH$_2$—),3.3–3.8(m,4H,—CH$_2$OCH$_2$—) 6.0–9.4(m,17H,methyne, olefin and aromatic H) | 0.22 ethyl acetate |

TABLE 3-continued

| Example | R | characteristic ¹H NMR signals (CDCl₃, 60 MHz), δ | Rf silica gel |
|---|---|---|---|
| 8e | (structure shown) | 1.1(d,6H,CH₃),3.3(s,2H, CH₂O),4.45(s,2H, CH₂OC₆H₅); 5.7(d,1H, CHOCO—),6.1–9.4(m,2H, aromat., olefin, protons) | 0.32 CH₂Cl₂/ MeOH = 20:1 |

EXAMPLE 9A

E,E-4-Pentyloxy-1-[4-(2-(3-pyridyl)ethenyl)phenyl]but-1-en-3-yl benzyl ether 70 mg (1.6 mmol) of a 55 percent NaH dispersion were initially introduced into 3 ml of dry dimethylformamide. At room temperature, 375 mg (1.1 mmol) of alcohol 7c in 3 ml of DMF were added, followed by 152 mg (1.2 mmol) of benzyl chloride in a little DMF. The mixture was stirred at room temperature for 18 h, water was added, and the mixture was extracted three times with toluene. Drying of the combined toluene phases over magnesium sulfate, removal of the solvent in vacuo and chromatography on silica gel (petroleum ether/ethyl acetate=2:1) produced 232 mg (0.5 mmol, 45%) of benzyl ether 9a as a colorless liquid.

¹H NMR (60 MHz, CDCl₃): =0.66–2.0 (m, 9H, —(CH₂)₃CH₃), 3.31–3.63 (m, 4H, —H₂COCH₂—), 3.91–4.0 (m, 1H, methyne H), 4.60 (d, 2H, —OCH₂Ph), 6.91–8.80 (m, 17H, olefinic and aromatic H).

Other compounds, inter alia Examples 9b–9f listed in Tab. 4, were obtained in analogy to Example 9a.

TABLE 4

| Example | R | characteristic ¹H NMR signals δ | Rf silica gel |
|---|---|---|---|
| | X = —CH=CH—,E | | |
| 9b | (structure shown, para) | 1,0–2,1(m,10H,cyclohexane methylen-H), 3,4(m,1H,methyne H),3,6(d,2H,OCH₂—), 4,2(m,1H,methyne H),4,6(d,2H, Ph—CH₂O—) | 0.48 ethyl acetate/ n-hexane = 7:3 |
| 9c | (structure shown, ortho) | 1,0–2,1(m,10H,cyclohexane methylen H), 3,4(m,1H,methyne H),3,5(d,2H,OCH₂—), 4,3(m,1H,methyne-H),4,6("s",2H, Ph—CH₂O—), | 0.20 ethyl acetate/ n-hexane = 7:3 |
| | X = —CH₂—CH₂— | | |
| 9d | (structure shown, para) | 0,7–1,9(m,9H,—(CH₂)₃CH₃),2,9("s",4H, —CH₂CH₂—),3,3–3,7(m,4H, —CH₂OCH₂—),4,0–4,7(m,1H, methyne H), 4,6("s",2H, —OCH₂Pyr) | 0,19 ethyl acetate/ n-hexane = 7:3 |

TABLE 4-continued

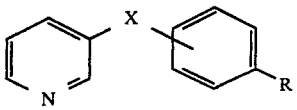

| Example | R | characteristic ¹H NMR signals δ | Rf silica gel |
|---|---|---|---|
| 9e | 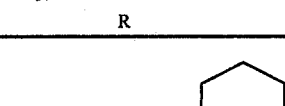<br>ortho | 1,0–2,0(m,10H,cyclohexane methylen-H), 3,4(m,1H,methyne H),2,9("s",4H, —CH₂CH₂—),3,6(d,2H,OCH₂—), 4,3(m,1H,methyne H),4,6("s"s,2H, PyrCH₂O—) | 0.20 ethyl acetate/ n-hexane = 7:3 |
| 9f | 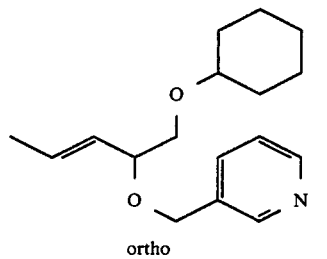<br>meta | 0,66–2,0(m,9H,—(CH₂)₃CH₃),3,3–3,6(m, 4H,—CH₂OCH₂—),3,9–4,4(m,1H, methyne H),4,6(d,2H,—OCH₂PH) | 0,51 ethyl acetate/ cyclohexane = 3:1 |

What is claimed is:
1. A compound of the formula I

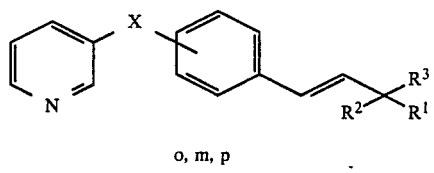

o, m, p in which:

X denotes a vinylene group or ethylene group,

R¹ and R² together with the carbon atom to which they are attached denote the carbonyl group, or R¹ denotes hydrogen and R² denotes the radical —OR⁴, in which R⁴ represents hydrogen or (a) a branched or unbranched aliphatic acyl radical having up to 10 carbon atoms, (b) the benzylcarbonyl or benzoyl radical, the phenyl radical being unsubstituted or substituted once to 3 times by halogen or C₁–C₄-alkyl, (c) the radical

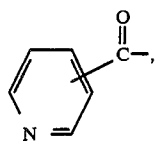

(d) branched or unbranched alkyl having 1–10 carbon atoms, (e) the benzyl radical, the phenyl nucleus being unsubstituted or substituted once to 3 times by halogen or C₁–C₄-alkyl, or (f) the radical

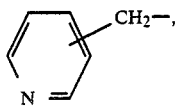

R³ denotes a phenyl radical which may be unsubstituted or substituted in the nucleus once to 3 times by one or more of halogen, trifluoromethyl, alkyl, alkoxy or said alkyl or alkoxy having 1–6 carbon atoms, or denotes an unsubstituted cycloaliphatic radical having 3–8 carbon atoms, or an unsubstituted straight-chain or branched unsaturated aliphatic hydrocarbon radical having 3–8 carbon atoms, or denotes a cycloaliphatic radical having 3–8 carbon atoms, a straight-chain or branched alkyl radical having up to 8 carbon atoms, or a straight-chain or branched unsaturated aliphatic hydrocarbon radical having 3–8 carbon atoms wherein the said cycloaliphatic, alkyl and unsaturated aliphatic radicals are substituted by (a) a straight-chain or branched alkoxy radical having up to 10 carbon atoms, or a straight-chain or branched alkenyloxy or alkynyloxy radical having 3 to 6 carbon atoms, (b) halogen, cycloalkyl having 3–7 carbon atoms, an unsubstituted phenyl, α- or β-thienyl or α- or β-furyl radical, or said phenyl, thienyl or furyl radical which is substituted in the nucleus once to 3 times by one or more of halogen, trifluoromethyl, alkyl or alkoxy, said alkyl or alkoxy having 1–6 carbon atoms, (c) an unsubstituted phenoxy, α- or β-thienyloxy or cycloalkoxy radical having 3–7 carbon atoms, or one of said radicals which is substituted in the nucleus once to 3 times by one or more of halogen, trifluoromethyl, alkyl or alkoxy, said alkyl or alkoxy each having 1–6 carbon atoms, or (d) a 1-imidazolyl radical.

2. A compound of the formula I as claimed in claim 1, in which
R¹ and R² together with the carbon atom to which they are attached denote the carbonyl group, or R¹ denotes hydrogen and R² denotes the radical —OR⁴, in which R⁴ represents hydrogen or
(a) branched or unbranched alkanoyl having up to 6 carbon atoms,
(b) the benzylcarbonyl or benzoyl radical, the phenyl radical being unsubstituted or substituted once by fluorine, chlorine or methyl,
(c) the radical

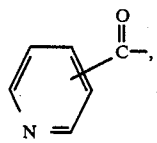

(d) branched or unbranched alkyl having 1–6 carbon atoms,
(e) the benzyl radical, the phenyl nucleus being unsubstituted or substituted once by chlorine, fluorine or methyl, or
(f) the radical

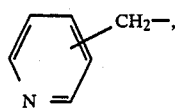

R³ denotes an unsubstituted cycloaliphatic radical having 3–8 carbon atoms, or an unsubstituted straight-chain or branched unsaturated aliphatic hydrocarbon radical having 3–8 carbon atoms, or denotes a cycloaliphatic radical having 3–8 carbon atoms, a straight-chain or branched unsaturated aliphatic hydrocarbon radical having 3–8 carbon atoms wherein the said cycloaliphatic, alkyl and unsaturated aliphatic radicals are substituted by
(a) a straight-chain or branched alkoxy radical having up to 6 carbon atoms, or a straight-chain or branched alkenyloxy or alkynyloxy radical having 3 to 6 carbon atoms,
(b) cycloalkyl having 3–7 carbon atoms, an unsubstituted phenyl, α- or β-thienyl or α- or β-furyl radical, or said phenyl, thienyl or furyl radical which is substituted in the nucleus once to 3 times by one of more of halogen, trifluoromethyl, alkyl or alkoxy, said alkyl or alkoxy having 1–6 carbon atoms,
(c) an unsubstituted phenoxy, α- or β-thienyloxy or cycloalkoxy radical having 3–7 carbon atoms, or one of said radicals which is substituted in the nucleus once to 3 times by one or more of halogen, trifluoromethyl, alkyl or alkoxy, said alkyl or alkoxy each having 1–4 carbon atoms, or
(d) a 1-imidazolyl radical.

3. A compound of the formula I as claimed in claim 1, in which R¹ and R² together with the carbon atom to which they are attached denote the carbonyl group, or R¹ denotes hydrogen and R² denotes the radical —OR⁴, in which R⁴ represents hydrogen, benzyl, alkyl having 1-6 carbon atoms, or the radical

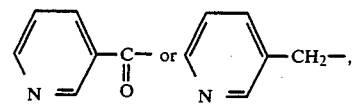

R³ denotes an unsubstituted cycloaliphatic radical having 3–8 carbon atoms, or an unsubstituted straight-chain or branched unsaturated aliphatic hydrocarbon radical having 3–8 carbon atoms, or denotes a cycloaliphatic radical having 3–8 carbon atoms, a straight-chain or branched alkyl radical having up to 8 carbon atoms, or a straight-chain or branched unsaturated aliphatic hydrocarbon radical having 3–8 carbon atoms wherein the said cycloaliphatic, alkyl and unsaturated aliphatic radicals are substituted by
(a) a straight-chain or branched alkoxy radical having up to 10 carbon atoms,
(b) cycloalkyl having 3–7 carbon atoms, an unsubstituted phenyl, α- or β-thienyl or α- or β-furyl radical, or said phenyl, thienyl or furyl radical which is substituted in the nucleus once to 3 times by one or more of halogen, trifluoromethyl, alkyl, alkoxy, said alkyl or alkoxy having 1–6 carbon atoms,
(c) an unsubstituted phenoxy, α- or β-thienyloxy or cycloalkoxy radical having 3–7 carbon atoms, or
(d) a 1-imidazolyl radical.

4. A pharmaceutical composition which contains a pharmaceutically effective amount of a compound of formula I as claimed in claim 1 together with a pharmaceutically acceptable vehicle.

5. A method for the treatment of disorders where there is an increased tendency of platelets to aggregate which comprises administering to a patient suffering from said disorders an effective amount of a pharmaceutical composition as claimed in claim 4.

6. A method for the treatment of disorders where there is an increased tendency of platelets to aggregate which comprises administering to a patient suffering from said disorders a pharmaceutically effective amount of a compound of formula I as claimed in claim 1.

* * * * *